(12) United States Patent
Bruno et al.

(10) Patent No.: US 8,134,020 B2
(45) Date of Patent: Mar. 13, 2012

(54) POLYMERIZATION OF HYDROXYTYROSOL MEDIATED BY HORSERADISH PEROXIDASES

(75) Inventors: Ferdinando F. Bruno, Andover, MA (US); Nicole Favreau, Waltham, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 92 days.

(21) Appl. No.: 12/634,856

(22) Filed: Dec. 10, 2009

(65) Prior Publication Data

US 2011/0144370 A1    Jun. 16, 2011

(51) Int. Cl.
C07C 303/00    (2006.01)
C07C 39/10    (2006.01)
C07C 69/76    (2006.01)

(52) U.S. Cl. .............................. 558/51; 568/763; 560/55

(58) Field of Classification Search .................. 514/405, 514/414, 421; 548/360.5, 453, 454
See application file for complete search history.

(56) References Cited

U.S. PATENT DOCUMENTS

| 7,098,246 | B2 | 8/2006 | Geelings et al. |
| 7,273,951 | B2 | 9/2007 | Biessen et al. |
| 2009/0035440 | A1 | 2/2009 | Velikov |
| 2009/0215881 | A1 | 8/2009 | Delaire et al. |

OTHER PUBLICATIONS

Macromolecules, (1995), vol. 28, p. 5192-5197.*
Lucia et al., Tetrahedron, vol. 62, (2006), p. 1273-1278, published online Nov. 10, 2005.*

* cited by examiner

*Primary Examiner* — Yong Chu
(74) *Attorney, Agent, or Firm* — Roger C. Phillips

(57) ABSTRACT

The present invention provides a method of producing polyhydroxytyrosol comprising the step of reacting hydroxytyrosol monomers or derivative thereof in a mixed solution comprising an enzyme, hydrogen peroxide, and an aqueous solvent.

4 Claims, 1 Drawing Sheet

POLYMERIZATION OF HYDROXYTYROSOL MEDIATED BY HORSERADISH PEROXIDASES

BACKGROUND OF THE INVENTION

1. Field of the Invention

The present invention relates generally to an enzymatic mediated polymerization process of hydroxytyrosol in an aqueous solvent which results in a novel polymer of polyphenol. This polymerized phenol exhibits improved electrical and optical properties, water solubility, and processability compared to phenolic resins and traditional phenols. It is synthesized using chemically safe and environmentally friendly conditions for use in a variety of applications including as an antioxidant for foods.

2. Description of the Related Art

Phenolic polymers, in particular phenol-formaldehyde resins such as novolaks and resols find wide application as wood composites laminates, foundry resins, abrasives, friction and molding materials, coatings and adhesives, fiber bonders and flame retardants. There has been a major concern, however, over the toxic effects of formaldehyde which are used in current art synthetic processes. In recent years there has been a tremendous surge towards the development of an alternative synthetic route, which circumvents the toxic effects of formaldehyde. Enzymatic polymerization of phenol in aqueous solutions was initially investigated as a possible benign and environmentally friendly solution to the synthesis of polyphenols (Akkara J. et al.). (J. A. Akkara, K. J. Senecal, and D. L. Kaplan, *Jour. of Pol. Sci.: Part A: Pol. Chem.,* 29, 1561, (1991)).

These initial attempts, however, were unsuccessful since only very low molecular weight oligomers could be formed which had limited useful properties to meet the requirements for such applications. Alternative enzymatic reactions have since been investigated to improve molecular weight and the mechanical, thermal, optical and electronic properties of these polymers; such as micelles, air-water interface monolayers and mixture into various organic solvents. Although the molecular weights and properties of these polyphenols were improved, their commercial application remained limited due to extensive branching and poor solubility and processability of the resulting polymers (Madhu Ayyagari, Kenneth A. Marx, Sukant K. Tripathy, Joseph A. Akkara, and David L. Kaplan: "Controlled Free-Radical Polymerization of Phenol Derivatives by Enzyme-Catalyzed Reactions in Organic Solvents" *Macromolecules* 1995, 28, 5192).

SUMMARY OF THE INVENTION

The approach described in this invention addresses these problematic issues and results in a new class of polyhydroxytyrosol which are prepared in aqueous medium using an environmentally safe, and facile "one-step" reaction. In addition, these polyhydroxytyrosol are water soluble with improved properties over the products made by known synthetic routes, based on factors including molecular weight, structural, thermal, mechanical, electronic and optical and processability. In this particular invention, enzymatic polymerization of hydroxytyrosol monomer was optimized by carrying out the reaction in the presence of an enzyme, and preferably an enzyme selected from the group consisting of horse radish peroxidase (HRP), laccase and pegylated hemadine. It is demonstrated in the present invention that a new class of polyphenols may be designed, synthesized and tuned, based on the type and position of functionalization of the monomer. The ease of synthesis and processability of this approach described in this invention will afford extensive opportunities to use these new polyphenols in a wide variety of industrial, medical, electronic, food and optical applications.

It is an objective of the present invention to provide a novel approach for the synthesis of a water soluble processable polyphenol with improved properties.

It is yet another objective of the present invention to provide an approach as described above which results in the production of a polyhydroxytyrosol which has enhanced water solublility, electronic and optical properties over natural polyflavonoids and polyphenols prepared using previously known art aqueous enzymatic synthetic routes.

It is yet another objective of the present invention to provide an approach as described above which results in the production of a water soluble form of a polyhydroxytyrosol. The synthetic route may be carried out under neutral or near neutral pH conditions without the use of any other toxic reagents.

It is yet another objective of the present invention to provide a simple (one step), environmentally safe and chemically mild synthetic route over previously known synthesis of a water soluble and processable polyflavonoids and polyphenols.

It is yet another objective of the present invention to provide an approach as described above which results in environmentally safe processing of these polyhydroxytyrosol into various architectures including but not limited to gels, coatings, paints, micelles, reversed micelles, thin films, fibers, chaff materials, electrostatic sprays, food antioxidant, medical drugs such as anticancer agents and membranes.

It is yet another objective of the present invention to provide an approach as described above which results in the synthesis of a polyhydroxytyrosol which may be used for applications including but not limited to wood composites laminates, foundry resins, abrasives, friction and molding materials, coatings and adhesives, fiber bonders and flame retardants light weight rechargeable batteries, rechargeable batteries, smart windows, chaff materials, and drug delivery systems.

Additional objectives, as well as features and advantages of the present invention, will be set forth in part in the description which follows, and in part will be obvious from the description or may be learned by practice of the invention. The objects, features and advantages of the present invention may be realized and attained by means of the instrumentalities and combinations particularly pointed out in the appended claims.

DETAILED DESCRIPTION OF THE PRESENTLY PREFERRED EMBODIMENTS

Accordingly, to achieve the foregoing objectives and in accordance with the purpose of the invention, as embodied and broadly described herein, a method for an enzymatic mediated polymerization of phenol substitute such as hydroxytyrosol comprises the preparation of a mixed solution containing a hydroxytyrosol and an oxidizing agent which is comprised of an enzyme (preferably horseradish peroxidase) and an electron acceptor (hydrogen peroxide), and an aqueous solvent. The procedure is a one-step, in situ reaction, which is highly selective and which produces minimal by-products and chemical waste. The resulting polymer solution can be immediately used as is or purified via techniques such as dialysis, centrifuging and precipitation and then used for subsequent processing strategies.

Preferably, the method of present invention is conducted in a mixed solution where the aqueous solvent comprises ethanol and water. Further, the method for enzymatic mediated polymerization is preferably conducted at a temperature of 5 to 37 C. Further, the amount of enzyme present during the polymerization is 0.4 to 2 mg/mL of the mixed solution, and the amount of hydrogen peroxide is 0.1 to 3% per volume of the mixed solution.

The polymerization is preferably conducted at a pH of the mixed solution of 4.3 to 8.5, more preferably 6.0 to 8.5.

Figure 1:
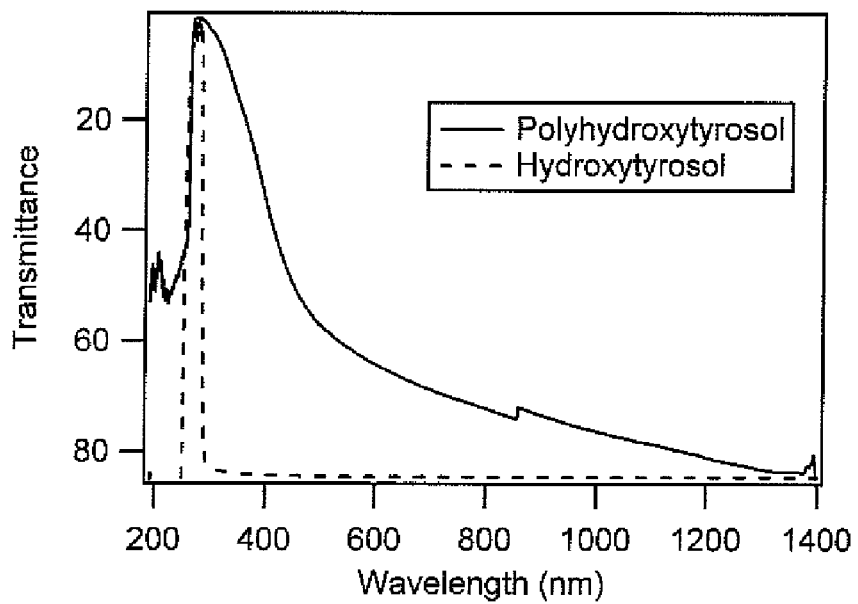
FIG. 1 shows the UV-vis absorption spectra of the polyhydroxytyrosol formed in presence of HRP and of the monomer.

FIG. 1 shows a comparison of the ultraviolet-visible absorption spectra of the polymerized hydroxytyrosol prepared with HRP with non-polymerized hydroxytyrosol. As shown in this figure, strong, broad absorption well out into the visible is observed for the polymerized sample. This absorption is indicative of extended conjugation found in polyphenol.

Since polyflavonoids prepared using previously known enzymatic strategies are difficult to process without using harsh, chemical modification or involved synthetic strategies, this new approach provides significant improvement in environmental compatibility, mild synthetic conditions, and environmentally safe processing opportunities for commercial application, such as in the food field.

The present invention provides a technique as described above which results in the synthesis of a polyphenol where the thermal, mechanical and electronic properties of the final complex can be tailored and optimized by judicious choice or modification of the monomer or co-monomers to be reacted.

These monomers may include, but are not limited to, various substituent groups at the ortho and meta positions to sterically control the orientation of the monomers with respect to the polyelectrolyte matrix during the polymerization. Functional groups could include but are not limited to methoxy, methyl, ethyl, sulfonate, carboxylate and hydroxyl groups. These functional groups can be in ortho or in metha position and they can be used as initiator or terminator of the polymeric chain.

Figure 2:
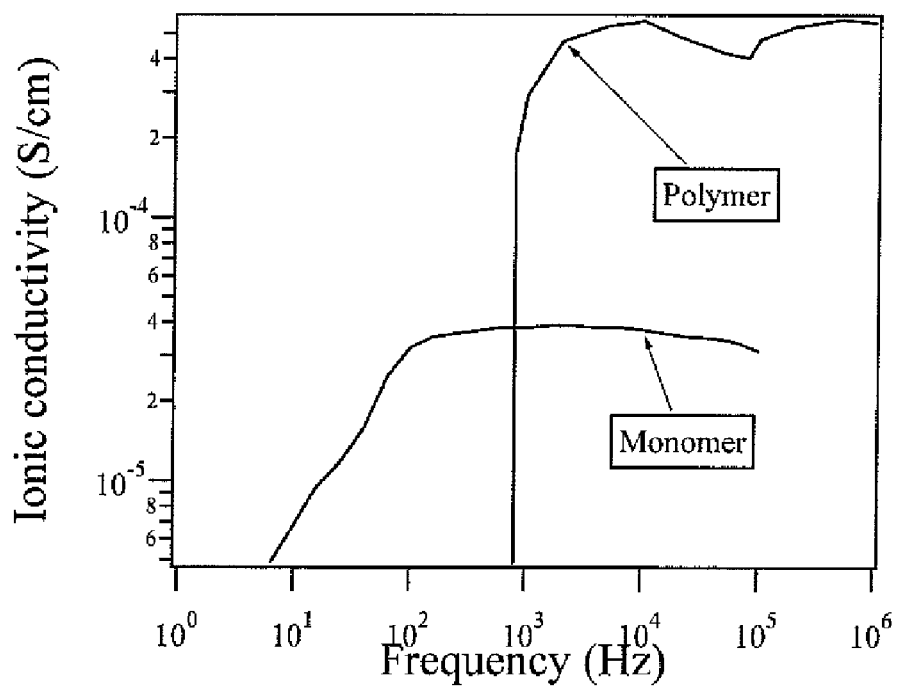
FIG. 2 shows the ionic conductivity in presence of 10 mM of LiCl of the polymer and monomer measured by an electronic cell.

The present invention provides a technique as described above which results in the synthesis of a polyhydroxytyrosol where the optical and electronic properties of the final complex can be tailored and optimized by judicious choice or modification of the solution pH or frequency. FIG. 1 shows the optical transmittance of the monomer reacted at pH of 1 at wavelength 600 nm (0.023) where the reaction does not happen because the enzyme at such low pH is totally inactive. In contrast, if the monomer is reacted at a pH of 7.5 at the same wavelength (600 nm) we have a transmittance of 68.7 signifying that the reaction has occurred. Moreover, ionic conductivity is demonstrated (FIG. 2) in presence of LiCl (10 mM). An ionic conductivity of $5.6*10^{-4}$ S/cm was found for the polymer. In comparison the monomer at the same frequency has an ionic conductivity of $3.8*10^{-5}$ S/cm. Electrical conductivity was not found for the polymer or monomer.

The polymers have sites for further modifications including, but not limited to, covalently coupling of other functionalities, thermal and UV crosslinkers and even biomolecules through simple coupling chemistry.

The polyhydroxytyrosol will allow for use in a wide range of applications including, but not limited to, wood composites laminates, foundry resins, abrasives, friction and molding materials, coatings and adhesives, fiber bonders and flame retardants light weight rechargeable batteries, rechargeable batteries, smart windows, chaff materials, food antioxidant, drugs for various health issues such as cancer and drug delivery systems.

The present invention is premised on the discovery that unsurpassed mild enzymatic synthesis is used in the described invention to prepare water soluble and processable polyhydroxytyrosol. Improved electronic and optical properties are obtained with the approach described in this invention. In addition, with judicious choice of matrix and/or monomer, the final polyflavonoid complex properties may be tailored to suit a wide range of industrial, electronic and optical applications.

Example 1

Hydroxytyrosol monomer polymerizes enzymatically in the presence of HRP activated by hydrogen peroxide to give a water soluble polyhydroxytyrosol.

Example 2

Hydroxytyrosol monomer polymerizes enzymatically in the presence of HRP, activated by hydrogen peroxide, in a solution composed of water/ethanol (80:20).

Example 3

Hydroxytyrosol monomer polymerizes enzymatically in the presence of HRP, activated by hydrogen peroxide, in a solution composed of water/ethanol (90:10).

Example 4

Hydroxytyrosol monomer polymerizes enzymatically in the presence of HRP, activated by hydrogen peroxide, in a solution composed of water/ethanol (70:30).

Example 5

Hydroxytyrosol monomer polymerizes enzymatically in the presence of HRP, activated by hydrogen peroxide, in a solution composed of water/ethanol maintained at pH raging between 6.0-8.5.

We claim:

1. A method of producing polyhydroxytyrosol, comprising reacting hydroxytyrosol monomers or derivatives of hydroxytyrosol monomers having functional groups selected from the group consisting of methoxy, methyl, ethyl, sulfonate, carboxylate and hydroxyl groups in a mixed solution consisting of an enzyme consisting of a horseradish peroxidase in the range of from about 0.4 mg/mL to about 2 mL of the mixed solution, hydrogen peroxide, and an aqueous solvent consisting of a water/ethanol mix from the group consisting of about 70:30, about 80:20 and about 90:10 to produce polyhydroxyrosol that has an absorbance in the ultra violet, visual and infra red frequency bands including an absorbance of about 0.1 at 1200 nanometers.

2. The method of claim 1 wherein the step of reacting hydroxytyrosol monomers is conducted at a temperature of 5 to 37° C.

3. The method of claim 1 wherein the pH of the mixed solution is 6.0 to 8.5.

4. The method of claim 1 wherein the pH of the mixed solution is 4.3 to 8.5.

* * * * *